United States Patent [19]

Paris et al.

[11] 4,046,887

[45] Sept. 6, 1977

[54] GLYCERIDES WITH ANTI-INFLAMMATORY PROPERTIES

[75] Inventors: Gerard Yvon Paris, Duvernay; Denis Gaston Cimon, Montreal, both of Canada

[73] Assignee: Abbott Laboratories, North Chicago, Ill.

[21] Appl. No.: 736,633

[22] Filed: Oct. 28, 1976

[51] Int. Cl.$^2$ .......................................... C07D 319/08
[52] U.S. Cl. ................................... 424/232; 260/340.2
[58] Field of Search ..................... 260/340.2; 424/232

[56] References Cited

U.S. PATENT DOCUMENTS

| | | | |
|---|---|---|---|
| 3,420,830 | 1/1969 | Fried | 260/340.2 |
| 3,741,985 | 6/1973 | Fried | 260/340.2 |

*Primary Examiner*—Norma S. Milestone
*Attorney, Agent, or Firm*—Paul D. Burgauer; Robert L. Niblack

[57] ABSTRACT

Triglycerides carrying hydrocarbon acyl moieties in the 1- and 3-positions and the 2-methyl-1,3-benzodioxan-4-on-2-yl moiety in the 2-position exhibit excellent anti-inflammatory properties.

12 Claims, No Drawings

GLYCERIDES WITH ANTI-INFLAMMATORY PROPERTIES

DETAILED DESCRIPTION OF THE INVENTION

Acetylsalicylic acid has been used with increasing frequency and amounts over the past 75 years for the treatment of pains and inflammations. It is an inexpensive, yet highly effective drug. Unfortunately, it has a side effect that makes its oral use dangerous or at least highly undesirable for many patients, those who have gastric or peptic ulcers or those who have gastric sensitivity.

It is an object of the present invention to provide an acetylsalicylic acid derivative that does not cause gastric irritation to patients who require anti-inflammatory therapy; it is a more particular object of the present invention to provide a pharmaceutically acceptable dosage form for an oral anti-inflammatory; it is another object to provide an oral dosage form of an anti-inflammatory which has the beneficial effect to acetylsalicylic acid without causing the above-mentioned side effects.

These and other objects are accomplished by providing an anti-inflammatory compound of the formula

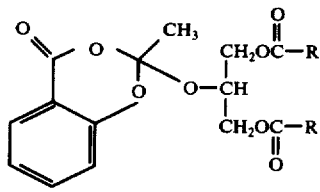

I wherein each R represents an alkyl group of 1-15 carbon atoms. This compound, for practical purpose, acts in the system of a warm-blooded animal like a pro-drug: the compound of formula I is of very low solubility in acid and water, but when it reaches the intestinal tract, absorption takes place without irritating the gut. A blood level of the drug, sufficient to alleviate pain and inflammation, can be attained without causing the gastric irritation often encountered when that same blood level is attained by administering acetylsalicyic acid.

Due to the water insolubility of I, the new compounds can be orally administered without the necessity of masking the taste.

As briefly mentioned above, the compounds of the present invention have unusual and surprising advantages over the compounds used by the prior art, namely the acetylsalicylic acid which is incorporated into the esters of this invention. These advantages primarily comprise the almost total absence of lesions observed in experimental animals and, translated into other mammals, clearly indicate the substantial absence of any type of irritation in the gastro-intestinal tract. At the same time, the new compounds can be administered in the same or larger doses in order to produce a higher blood level of the anti-inflammatory component to enter the blood stream and/or lymphatic system as a triglyceride; however, it is believed that for the brief moment of the molecule's passage through the membrane of the mucosa, the ester groups in the 1- and 3-positions are temporarily lost with prompt re-esterification within the mucosal cells and later in the blood or lymph system. This is of particular interest because anti-inflammatories usually have to be given on a permanent or semi-permanent basis which in the past has often led to serious damage in the gastro-intestinal tract of the consumer, causing irritation or intestinal bleedings as well as activating or reactivating ulcers. It is thus of particular interest to observe that with the triglyceride of the present invention, a known anti-inflammatory can be administered over extended periods of time without irritation; it is capable of producing prolonged or semi-permanent levels of the new active principle in the blood stream above the minimum effective level yet without ever surpassing, reaching or even approaching the toxic level.

Compounds made in this fashion can easily be compounded into dosage unit form for medicinal use. For instance, pharmaceutical tablets can be prepared by mixing I with the usual type of adjuvants, flavoring agents, fillers, buffers and/or coloring agents which together with a lubricant can be compressed into the usual tablets. Also, a mixture of the above active compound with fillers and/or buffers or solid diluents can be processed into wafers, pills, or just simply filled into gelatin capsules in dosages of suitable amounts. Preferably, a dosage unit contains between 30 and 1000 mg. of I, and if desired, other drugs can be admixed therewith.

In a general embodiment, the compounds of formula I are made by reacting a 1,3-glycerol diacyl ester with acetylsalicyloyl chloride in the presence of an inert, organic reaction medium at a temperature between room temperature and the boiling point of the reaction mixture. For practical purposes, temperatures of >100° C. are not desirable as the co-reactants combine easily at ambient temperatures. Among the preferred reaction media are chloroform or carbon tetrachloride; however, nitrobenzene, chlorobenzene, dichlorobenzene, benzene or paraffines are also well suited. The term "inert" is used in this regard primarily to indicate that the solvent does not react with either of the two reactants or with the formed end product.

The above acyl moieties extend from the simple acetyl to the hexadecanoyl groups. In general, those containing an even number of total carbon atoms are advantageous to be used, i.e., acetyl, butyryl, hexanoyl, octanoyl, dodecanoyl, palmitoyl and the like.

In order to illustrate the method for preparing and using the new triglycerides, reference is made to the following examples which, however, are not meant to limit the invention in any way. In all instances, the described new products were found to conform with the expected nmr, mass spectrum and their calculated values for the chemical microanalyses.

EXAMPLE 1 a. Dihydroxyacetone dimer is dried for 4 hours in a vacuum pistol at 50° C; 13 g. of the dry material is then suspended in 500 ml. of dry, ethanol-free chloroform in a 1-liter round-bottomed three-neck flask equipped with a calcium chloride drying tube and a pressure-equalizing dropping funnel. To this suspension at 5° C. is added 25 ml. of dry pyridine. The mixture is cooled in an ice bath while 76 g. of freshly distilled palmitoyl chloride is added dropwise over 1 hour. The reaction mixture is stirred at room temperature overnight. The precipitate of pyridine hydrochloride is filtered off and the chloroform solution is washed with 100 ml. portions of water. The chloroform solution is then evaporated to give a gummy solid which is triturated with a small amount of diethyl ether and filtered to give 52.2 g. of a white solid identified as 1,3-dipalmitoyloxy-2-propanone, melting at 79° – 82° C. and obtained in a yield of 64% of theory.

b. In a three-liter Erlenmeyer flask, 50.2 g. of the above compound is suspended in 1100 ml. of tetrahydrofuran and 250 ml. of benzene using mechanical stirring. The mixture is cooled to 5° C. and 70 ml. of water is added. The mixture is stirred and 5.02 g. of neutral sodium borohydride (made by stirring commercial sodium borohydride in ethyl acetate overnight, washing with ether and drying) in 0.5 g. quantities followed by stirring the suspension at 5° for 45 minutes. At this time, 2.5 ml. of glacial acetic acid is added slowly to destroy excess borohydride and the mixture is stirred for 30 minutes at 5° C., before 300 ml. each of chloroform and diethyl ether are added. The mixture is washed with two 250 ml. portions of water and subsequently with 250 ml. of a 1% sodium bicarbonate solution. The organic layer is then dried over anhydrous magnesium sulfate and evaporated to give a gummy solid. This material is triturated with a small amount of acetone and filtered to give 44.4 g. (88%) of 1,3-dipalmitoyloxy-2-propanol as a white solid melting at 71°–73° C.

c. A solution of 2.84 g. of 1,3-dipalmitoyloxy-2-propanol, 0.992 g. of acetylsalicyloyl chloride, 0.44 ml. of dry pyridine and 80 ml. of dry chloroform is heated to a gentle reflux for 15 hrs. The reaction is then washed with 50 ml. each of water (twice), with 1% aqueous hydrochloric acid (twice), with water, with 1% aqueous sodium bicarbonate (twice), with water (twice) and 75 ml. of brine. The organic phase is dried over anhydrous sodium sulfate and evaporated. The resulting waxy solid is crystallized from petroleum ether (b. range 30°-60° C), while treating it with activated charcoal, to yield 1.32 g. (36% of theory) of 1,3-dipalmitoyloxy-2(2-methyl-1,3-benzodioxan-4-on-2-yloxy) propane.

EXAMPLE 2

By following the procedure of Example 1(a) and (b), using 11.6 g. of the dihydroxyacetone and 58.2 g. of didecanoyl chloride, 48.2 g. of 1,3-didecanoyloxy-2-propanol is obtained. This material (10 g.) is refluxed with 4.96 g. of acetylsalicyloyl chloride and 2.2 ml. of pyridine in 300 ml. of dry chloroform for 24 hrs. The reaction mixture is treated with 100 ml. of water; the chloroform layer is washed with 100 ml. of 1% hydrochloric acid, 100 ml. of 1% aqueous sodium carbonate and, finally, twice with 100 ml. of water. After drying the chloroform layer over magnesium sulfate, it is evaporated to dryness and purified over a previously deactivated, 500 g. silica gel column. Elution with petroleum ether/ether 85.15 yields 4.8 g. (31% of theory) of 1,3-didecanoyloxy-2(2-metyl-1,3-benzodioxan-4-on-2-yloxy) propane.

EXAMPLE 3

A solution of 0.88 g. of 1,3-diacetoxy-2-propanol and 0.99 g. of acetylsalicyloyl chloride in 40 ml. of chloroform is heated to a gentle reflux for 15 hrs. The mixture is then evaporated and the residue is dissolved in 150 ml. of ether. The reaction mixture is washed with 2% aqueous sodium bicarbonate (2 ×25 ml.) and dried over anhydrous sodium sulfate. Evaporation yields 1.1 g. of white 1,3-diacetoxy-2-(2-methyl-1,3-benzodioxan-4-on-2-yloxy propane (65% of theory), melting at 66.5°–67.0° C.

When the chloroform/pyridine used above is replaced by carbon tetrachloride, the resulting product represents a 1:1 mixture of the above product and the 1,3-diacetoxy-2-(2-acetyl)salicyloyloxy propane. Both of these materials have similar pharmacological action as they both work as analgesics and anti-inflammatories upon oral administration of a therapeutic dose thereof.

EXAMPLE 4

The compound of Example 2 was tested for its ability to reduce the swelling of artificially induced edema in rat paws caused by carageenan injection according to the procedure of Winter et al, Proc. Soc. Exp. Biol. Med., 111, 544 (1962). Two hours after administering 100 and 400 mg/kg., respectively of I (R = $C_9H_{19}$) by stomach gavage, 0.1 ml. of a 1.5% carageenan solution in saline was administered by subplantar injection to a group of 6 rats which had been fasted for 18 hours (water ad lib.). With the indicated doses, a 30% and 46% edema inhibition, respectively, was found over the values established with control animals.

The animals treated with 400 mg/kg were subsequently sacrificed to check them for lesions in the gastro-intestinal tract. None of the six animals showed any lesions, while a group of 6 control animals receiving 80 mg.kg of acetylsalicylic acid (1/5 of the dose of compound I) showed (2) animals with stomach lesions.

EXAMPLE 5

In a test using approximately the same mole/kg. dose carried out according to Example 4, the compounds of Examples 1 and 3 were also compared to a control vehicle made up in the same fashion as the test vehicles. With the compound of Example 1 at a dose of 345 mg/kg (472$\mu$M/kg) and the compound of Example 3 at a dose of 160 mg/kg (473$\mu$M/kg), the average paw size measured 3 hrs. after injection of carrageenin was 14.5% less than the control for both test compounds.

In order to show the need of the glyceride moiety, the same test was also carried out with 2-hexadecyloxy-2-methyl-1,3-benzodioxan-4-one (190 mg/kg or 470 $\mu$M/kg) and acetylsalicylic acid (85 mg/kg or 472 $\mu$M/kg). The anti-edema activity of these "control" samples were 0 and 17.4%, respectively, when averaged over 1 hour and 3 hour readings. On this scale, the compounds of Examples 1 and 3 both show a 14.5% anti-edema activity.

In view of the extremely low toxicity of the above triglycerides of structure I and the extremely low incidence of lesions and gastric irritations, the new compounds are of great value in the treatment of inflammation and edema. They can be administered over extended periods of time without danger of gastric or intestinal bleedings, ulcers or the milder forms of irritations and upsets as is often the case with the free acids currently used as anti-inflammatories. The new compounds have extremely favorable therapeutic index values as in most instances, no toxicity could be established even with massive doses.

It will be obvious to those skilled in the art that the dosage of the new triglyceride depends, to a large extent, on the type esters used for the 1- or 3-positions When R is a small moiety, i.e. contains 1, 3 or 5 carbon atoms, the molecule is much smaller than when R contains 13 or 15 carbons. Thus, the total daily does or single effective dose to be administered must be adjusted to the molecular weight of I, since in all instances, the active principle remains the same.

In order to prepare capsules for oral administration, the following procedure is employed: 25 g. of the compound of Example 1 is preblended with 212.5 g. of lactose and 12.5 g. of talcum powder. The preblend is passed through a suitable screen and the screened powder is then blended and filled into gelatin capsules No. 3 to produce a filled weight of 250 mg. per capsule.

The following is a typical tablet formula which may be used to incorporate the compunds of the present invention into tablet form. 13 g. of corn starch, 50 g. of I, 132 g. of calcium phosphate dibasic dihydrate, 1 g. of magnesium stearate and 4 g. of talcum powder with water q. s. to 200 g. Part of the above corn starch is milled together with the active drug and the calcium phosphate; this blend is milled and passed through a 40-mesh screen. The remaining portion of the corn starch is granulated with water, heated and mixed with the above blend in a hot air oven at 50° C. and sifted through a 16-mesh screen. The talcum powder and magnesium stearate are then added, the mixture is blended and subsequently passed through a 30-mesh screen and blended for at least 15 minutes. In order to prepare tablets, this mixture is compressed using a 9/32" standard convex punch producing a tablet of hardness 7-9 with each tablet weighing 200 mg. and containing 50 mg. of the active drug.

Of course, other pharmaceutically acceptable compositions can easily be prepared, e.g., suspensions, syrups pills, wafers, and the like, preferably containing a predetermined amount of the active ingredient per given volume of such a dosage form. In case of liquid preparations for oral ingestion, a suitable non-toxic vehicle is used containing the necessary flavoring and sweetening agents to make up a liquid that is pleasant in taste and mouth feel.

What is claimed is:

1. A compound of the formula

I

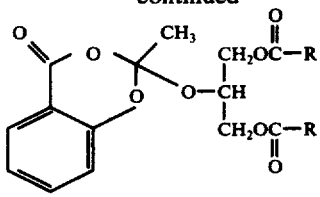

-continued

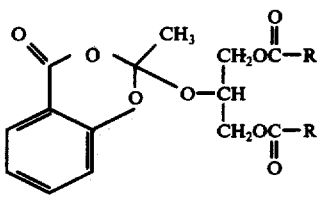

wherein each R is an alkyl group of 1-15 carbon atoms.
2. The compound of claim 1 wherein R is methyl.
3. The compound of claim 1 wherein R is pentadecyl.
4. The compound of claim 1 wherein R is nonyl.
5. The process of preparing the compound of claim 1, comprising condensing acetylsalicyloyl chloride with a glycerol diester of the formula ROCOCH$_2$CHOHCH$_2$OCOR wherein R is an alkyl of 1-15 carbon atoms in the presence of an inert, organic solvent at a temperature between room temperature and the boiling point of the reaction mixture.
6. The process of claim 5 wherein R is methyl.
7. The process of claim 5 wherein R is pentadecyl.
8. The process of claim 5 wherein R is nonyl.
9. The process of claim 5 wherein said inert solvent is chloroform.
10. The process of claim 5 wherein said inert solvent is carbon tetrachloride.
11. An anti-inflammatory composition containing an effective amount to combat inflammation in warm-blooded animals afflicted therewith, of the compound of formula

I wherein R is an alkyl group of 1-15 carbon atoms together with and acceptable pharmaceutical carrier in dosage unit form.
12. The composition of claim 1 wherein said dosage form is a tablet.

* * * * *